United States Patent [19]
Rayborn

[11] Patent Number: 6,111,146
[45] Date of Patent: Aug. 29, 2000

[54] ALKYL CYCLOHEXANOL ALKOXYLATES AND METHOD FOR MAKING SAME

[76] Inventor: Randy L. Rayborn, 5200 Park Rd. Suite 120, Charlotte, N.C. 28209

[21] Appl. No.: 08/922,914

[22] Filed: Sep. 3, 1997

[51] Int. Cl.[7] .................................................... C07C 43/11
[52] U.S. Cl. ............................................................. 568/606
[58] Field of Search ............................................. 568/606

[56] References Cited

U.S. PATENT DOCUMENTS

| | | |
|---|---|---|
| 2,174,761 | 10/1939 | Schuette et al. . |
| 2,213,477 | 9/1940 | Steindorff et al. . |
| 2,674,691 | 4/1954 | Lundsted . |
| 2,677,700 | 5/1954 | Jackson et al. . |
| 3,152,998 | 10/1964 | Moss . |
| 3,336,241 | 8/1967 | Shokal . |
| 3,859,322 | 1/1975 | Buckman et al. . |
| 3,859,324 | 1/1975 | Bloch . |
| 3,953,522 | 4/1976 | Bloch . |
| 3,953,523 | 4/1976 | Bloc . |
| 3,997,621 | 12/1976 | Brennan . |
| 3,997,622 | 12/1976 | Isa et al. . |
| 4,013,736 | 3/1977 | Woo . |
| 4,045,508 | 8/1977 | Cupples et al. . |
| 4,210,764 | 7/1980 | Yang et al. . |
| 4,223,164 | 9/1980 | Yang et al. . |
| 4,239,917 | 12/1980 | Yang . |
| 4,280,919 | 7/1981 | Stoeckigt et al. . |
| 4,302,613 | 11/1981 | Yang et al. . |
| 4,317,940 | 3/1982 | Scardera et al. . |
| 4,453,022 | 6/1984 | McCain et al. . |
| 4,472,550 | 9/1984 | Reiff et al. . |
| 4,504,412 | 3/1985 | Harris ........................................ 252/522 |
| 4,533,486 | 8/1985 | Scardera et al. . |
| 4,754,075 | 6/1988 | Knopf et al. . |
| 4,866,201 | 9/1989 | Motojima et al. . |
| 4,965,014 | 10/1990 | Jeschke et al. . |
| 5,015,787 | 5/1991 | Van Peppen . |
| 5,112,519 | 5/1992 | Giacobbe et al. . |
| 5,362,913 | 11/1994 | Knifton et al. . |
| 5,395,976 | 3/1995 | Scharschmidt et al. . |
| 5,460,750 | 10/1995 | Diaz-Arauzo . |
| 5,530,147 | 6/1996 | Wettling et al. . |
| 5,576,281 | 11/1996 | Bunch et al. . |

FOREIGN PATENT DOCUMENTS

| | | |
|---|---|---|
| 0 467 290 A2 | 7/1991 | European Pat. Off. . |
| 753 258 A2 | 1/1997 | European Pat. Off. . |
| 2 354 989 | 6/1977 | France . |
| 44 17 947 A1 | 11/1995 | Germany . |

*Primary Examiner*—Michael L. Shippen
*Attorney, Agent, or Firm*—Dority & Manning, P.A.

[57] ABSTRACT

The invention is a new family of non-ionic surfactants and a method of making same. The surfactants are made by (1) alkoxylating an alkylphenol with an alkylene oxide using a standard alkylene catalyst; (2) hydrogenating the alkoxylated alkylphenol until it is either fully or partially saturated using selective catalysts such that the aromaticity of the compound is eliminated; (3) if necessary, further alkoxylating the resulting non-aromatic molecule. The resulting compound is an alkylcyclohexanol alkoxylate possessing excellent surfactant properties for use as a emulsifiers, for wetting and penetration, for scouring, and general surface modification.

52 Claims, No Drawings

ALKYL CYCLOHEXANOL ALKOXYLATES AND METHOD FOR MAKING SAME

BACKGROUND OF THE INVENTION

The invention relates a new family of non-ionic surfactants and, more specifically, to alkyl cyclohexanol alkoxylates and a method for making same.

Non-ionic surface active agents and their preparation are generally known in the art. U.S. Pat. Nos. 2,174,761; 2,674,619; and 2,677,700 teach non-ionic surfactant compositions prepared by the addition of ethylene oxide and propylene oxide to a reactive hydrogen compound. It is known in the art to make non-ionic surfactants from numerous starting hydrophobes, such as alkylated phenols, fatty alcohols, fatty acids, etc. This family of surfactants has numerous end uses, such as foam control agents, wetting agents, scouring agents for cleaning formulations, emulsifiers, de-emulsifiers, dispersants, synthetic lubricants, and any application where surfactantcy, lubricity, and foam control are important. Ethoxylated nonylphenol, in particular the nine to twelve mole ethoxylate, has achieved a dominant position in the worldwide surfactant market as the non-ionic surfactant of choice because of its excellent surfactant properties, low odor, ease of use due to lower pour points and lower chill points, and low costs compared to other non-ionic surfactants.

In the recent years, alkylphenol alkoxylates, such as ethoxylated nonylphenol, have been criticized for having poor biodegradability, high aquatic toxicity of the byproducts of the biodegradation of the phenol portion, and there is an increasing concern that these chemicals act as endocrine disrupters. Some studies have shown there to be links between alkylphenols and declining sperm count in human males and there is evidence that alkylphenols may harmfully disrupt the activity of human estrogen and androgen receptors.

Concern over the environmental and health impact of alkoxylated alkylphenols has led to governmental restriction on the use of these surfactants in Europe, as well as voluntary industrial restrictions in the United States. Many industries have attempted to replace these preferred alkoxylated alkylphenol surfactants with alkoxylated linear and branched alkyl primary and secondary alcohols, but have encountered problems with odor, performance, formulating, and increased costs. The odor and some of the performance difficulties of the alkoxylated alkyl alcohols are related to the residual free alcohol, which is the portion of the reactant alcohol that does not react with alkylene oxide during the alkoxylation step.

The presence of the unreacted free alcohol is due to the reaction kinetics of alkoxylating an alcohol under a base catalysis in which a nucleophilic attack by $RO^-$ occurs at a ring carbon atom of the alkylene oxide. For example, the product distribution of ethoxylating under basic conditions is determined by the relative rates of two steps and the relative acidities of the alcohol and its ethylene oxide adducts.

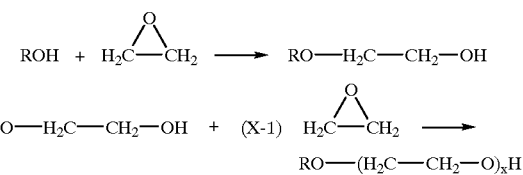

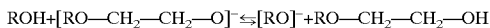

This relative acidity becomes important in determining the equilibrium constant for the proton exchange reaction between the starting alcohol and its ethylene oxide adducts.

$$ROH + [RO-CH_2-CH_2-O]^- \rightleftharpoons [RO]^- + RO-CH_2-CH_2-OH$$

When the acidity of ROH is slightly less than that of its corresponding oxide adduct, such as with a linear or branched alkyl alcohol, the equilibrium constant for the proton exchange reaction will be less than or equal to 1. Because formation of any specific anion is not strongly favored, the chain extension of the alcohol oxide adduct will occur well before the original ROH undergoes reaction.

When the acidity of ROH is greater than that of its corresponding oxide adduct, such as with a phenol, the equilibrium constant for the proton exchange reaction will be much larger than 1. Even when there is an excess of ethylene oxide, chain extension does not occur until substantially all of the ROH has reacted to form the monoadduct. Aqueous acid ionization constants for various alcohols and their adducts are approximately $10^{-9}$ for phenol, $10^{-15}$ for phenol ethylene oxide adducts, $10^{-16}$ for alkyl alcohols and $10^{-15}$ for alkyl alcohol ethylene oxide adducts.

The impact of the equilibrium constant for the proton exchange reaction could result in 15% to 40% unreacted alcohol in a linear primary or secondary alcohol system even after four moles of ethylene oxide (EO) have been reacted. This residual "free alcohol" not only negatively impacts the surfactant and formulating properties of an alkoxylated alkyl alcohol but increases irritation of eyes and skin associated therewith and gives the alkoxylated alkyl alcohol the strong offensive odor of the starting alcohol. Efforts to resolve these problems are taught in U.S. Pat. No. 4,210,764, in which BaO and cresylic acid are used as the catalyst system; U.S. Pat. No. 4,223,164, in which basic compounds of strontium in the presence of phenol are used as the catalyst; U.S. Pat. No. 4,453,022, in which $Ca(OEt)_2$ is the catalyst; and U.S. Pat. No. 4,754,075, in which CaO and an activator, such as a glycol, is the catalyst system in which the ethoxylation of alkyl alcohols results in narrow range or peaked ethoxylates. These peaked or narrow range ethoxylated alcohols, with lower levels of free alcohol, show some improvement in overall surfactant properties, but problems of odor, high cost, and ease of formulating still remain a problem.

Typical capillary GC results to determine the percentage of free alcohol on a one, four, and six mole ethoxylate of a nonylphenol using a basic catalyst, of a lauryl alcohol using a basic catalyst, and of a lauryl alcohol using a "peaking" catalyst are as follows:

TABLE 1

| Hydrophobe/ Catalyst | % FREE ALCOHOL | | |
|---|---|---|---|
| | One mole Ethylene Oxide | Four mole Ethylene Oxide | Six mole Ethylene Oxide |
| Nonylphenol/ NaOH | 0.05 | 0.01 | <0.01 |
| Lauryl Alcohol/ NaOH | 64.5 | 23.2 | 13.8 |
| Lauryl Alcohol/ CaO (peaking) | 21.5 | 8.1 | 5.2 |

Other approaches to produce environmentally friendly, low odor, non-endocrine disrupting surfactants include use of alkyl polyglycosides, glucoamine, carboxylated nonionics, ethoxylated amines, amphoterics, and N-methyl glucosamide. Although these approaches have achieved improved ecological, non-endocrine disrupting properties, the overall surfactant properties are generally poor, formulating is difficult, and costs are anywhere from 20% to 150% higher than costs associated with using alkylphenol alkoxylates.

Other methods to produce environmentally friendly surfactants are discussed in U.S. Pat. Nos. 3,859,324, 3,953,522, and 3,953,523, in which methods are shown to produce n-alkyl substituted hydroxypolyalkoxymethylcyclohexenes and n-alkyl substituted hydroxypolyalkoxymethylcyclohexanes. These methods involve a Diels-Alder condensation of butadiene with allyl alcohol. The resulting hydroxymethylcyclohexene is then placed in the presence of a free radical generating compound alkylated with an alpha olefin to form an alkyl substituted hydroxymethylcyclohexene, which is then hydrogenated and alkoxylated to form a nonionic surfactant. However, the performance of the resulting nonionic product not only suffers from problems associated with a large percentage of unalkoxylated n-alkyl substituted hydroxymethylcyclohexane, but the process of alkylation will also yield a large percentage of polyalphaolefins, which are highly branched hydrocarbons, that negatively impact surfactant properties.

SUMMARY OF THE INVENTION

It is an object of the present invention to provide a surfactant with improved biodegradability, reduced toxicity of the biodegradation byproducts, and reduce interference with human endocrines. It is also an object of the present invention to produce such a surfactant that reduces or eliminates problems encountered with odor, performance, formulating, and cost.

In carrying out these and other objects of the invention, there is provided a compound having the formula:

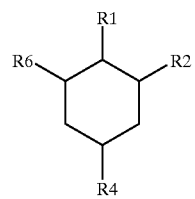

with R2, R4, and R6 being each independently selected from hydrogen; an alkyl, alkenyl, or alkynyl group or mixtures thereof having between one and thirty carbons; —$C_6H_{11}$; and —$C_8H_{15}$, and R1 is an oxypolyalkylene oxide having the formula:

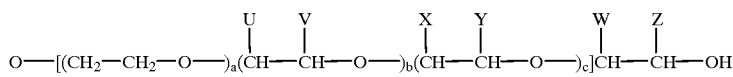

Where:
U is hydrogen or $CH_3$—,
V is $CH_3$— if U is hydrogen, or hydrogen if U is $CH_3$—,
X is hydrogen or $CH_3CH_2$—,
Y is $CH_3CH_2$—if X is hydrogen, or hydrogen if X is $CH_3CH_2$—,
W is hydrogen, $CH_3$—, or $CH_3CH_2$—,
Z is hydrogen, $CH_3$—, or $CH_3CH_2$— if W is a hydrogen, or hydrogen if W is $CH_3$— or $CH_3CH_2$—,
a is an integer between 0 and 200,
b is an integer between 0 and 100,
c is an integer between 0 and 100, and
a+b+c=2–200.

The invention also includes a process for preparing such an alkylcyclohexanol alkoxylate by
alkoxylating an alkylphenol by reacting

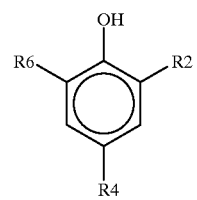

with R2, R4, and R6 being each independently selected from hydrogen; an alkyl, alkenyl, or alkynyl group or mixtures thereof having between one and thirty carbons; —$C_6H_5$; and —$C_8H_9$,
with an alkylene oxide, such as ethylene oxide, propylene oxide, butylene oxide, and mixtures thereof to alkoxylate the phenol, resulting in a compound having the formula:

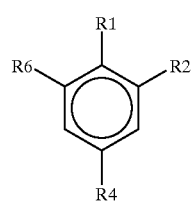

with R2, R4, and R6 being each independently selected from hydrogen; an alkyl, alkenyl, or alkenyl group or mixture thereof having between one and thirty carbons, —$C_6H_5$; and —$C_8H_9$,
R1 as recited above; and
hydrogenating the resulting alkoxylated alkylphenol.

The alkoxylation step results in less than 2% free alkylphenol and the hydrogenation step results in at least 90% saturation of the aromatic ring.

DESCRIPTION OF THE PREFERRED EMBODIMENT

An alkylphenol of the structure

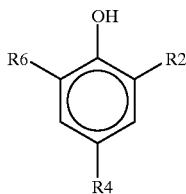

where R2 R4, and R6 are each independently either hydrogen; an alkyl, alkenyl, or alkynyl group or mixtures thereof having between one and thirty carbons; —$C_6H_5$; or —$C_8H_9$ is reacted with an alkylene oxide, such as ethylene oxide, propylene oxide, or butylene oxide, to form a low residual homopolymer, copolymer, or terpolymer using techniques known by those skilled in the art. These techniques include those using alkylene catalysts NaOH, $NaOCH_3$, KOH, MgO, CaO, etc., at temperatures ranging from 50° C. to 160° C. under pressures from 25 psi to 120 psi. Such reaction results in a small amount of free alkylphenols (unreacted with alkylene oxide) because of the high acidity of the phenol, as discussed above.

This reaction results in a product described by the general structure

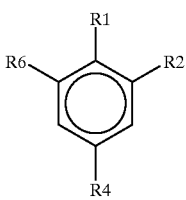

R2, R4, and R6 as recited above, and R1 being an oxypolyalkylene oxide of the general formula

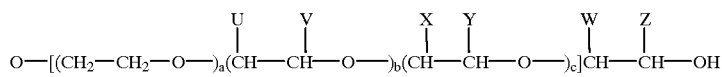

Where:
U is hydrogen or $CH_3$—,
V is $CH_3$— if U is hydrogen, or hydrogen if U is $CH_3$—,
X is hydrogen or $CH_3CH_2$—,
Y is $CH_3CH_2$— if X is hydrogen, or hydrogen if X is $CH_3CH_2$—,
W is hydrogen, $CH_3$—, or $CH_3CH_2$—,
Z is hydrogen, $CH_3$—, or $CH_3CH_2$— if W is a hydrogen, or hydrogen if W is $CH_3$— or $CH_3CH_2$—,
a is an integer between 0 and 200,
b is an integer between 0 and 100,
c is an integer between 0 and 100, and
a+b+c=2–200.

Note that if unsaturated hydrocarbon radicals, such as alkenyl or alkynyl structures, are present on the ring, these radicals will be saturated to alkyl radicals during the hydrogenation step described below. It is preferable that the hydrocarbon radicals present on the ring be saturated hydrocarbon radicals.

It is also preferable that the alkylphenol be alkylated with a straight-chain alkyl group in the para position having between eight and twelve carbons, inclusive, and hydrogen in the R2 and R6 positions. It is noted that most commercial alkylphenols have branched, and not linear, alkyl chains, but linear chains are preferable. It is more preferable that the alkyl group be either an octyl or nonyl group, most preferably, a nonyl group.

When alkoxylating the alkylphenol, it is preferable that ethylene oxide be used as the alkoxylate and that between four and twenty moles ethylene oxide be used. More preferably, between six and twelve moles of ethylene oxide are used and, most preferably, nine moles of ethylene oxide are used. It is preferable that the alkoxylation product have less than about 2% free alkylphenol.

The resulting alkoxylated alkylphenol is then hydrogenated using techniques known by those skilled in the art, such as taught in U.S. Pat. No. 3,336,241, in which the aromatic compound is hydrogenated with a catalyst, such as rhodium or ruthenium metal, supported on an inert carrier, such as carbon, at temperatures of 30° C. to 100° C., or using the technique taught in U.S. Pat. No. 5,530,147, in which a ruthenium compound produced as described in the patent is mixed with the aromatic alkoxylate and then hydrogenated at pressures of 200 bar to 310 bar and temperatures of 40° C. to 70° C. Other techniques for hydrogenation are taught in U.S. Pat. Nos. 4,045,508, 4,013,736, 3,997,622, 3,997,621, and 3,152,998 and can also be utilized with a number of metal catalysts suitable for hydrogenation, such as nickel, platinum, palladium, copper, and Rainey nickel supported on a variety of porous materials, such as alumina, charcoal, or kieselguhr. It is necessary to ensure that the degree of saturation resulting from the hydrogenation be as high as possible, preferably at least about 90%, in order to ensure as complete destruction of the aromatic ring as possible in order to achieve improved biodegradability, low aquatic toxicity, and no endocrine disruption.

The resulting alkoxylated alkyl cyclohexanol product can be further reacted with an alkylene oxide to improve productivity of the hydrogenation and alkoxylation processes or conventional peaking techniques can be used to produce a narrow range ethoxylate. It is preferable that the hydrogenation product have less than about 10% unsaturated aromaticity.

If it were to be attempted to produce similar compounds by hydrogenation of an alkylphenol and then subsequent alkoxylation, the properties of the products produced in this manner have a much stronger odor, increased difficulty to formulate with other compounds, and poorer performance due to the large amount of residual unalkoxylated alkyl cyclohexanol (free alcohol), which can be as high as 45% when reacted with four moles of an alkylene oxide. This high level of unreacted alcohol is due to the extremely low acidity of the proton and stearic hindrance of the hydroxyl of the alkyl cyclohexanol.

The compound and process of the present invention results in products possessing excellent surfactancy with good low temperature properties and low odor while improving the ecological impact and reducing the estrogen mimicking and endocrine disruption potential of their alkoxylated alkylphenol counterpart.

The following examples serve to illustrate the invention without restricting it in any way.

EXAMPLE 1

NONYLPHENOL (EO)$_9$, HYDROGENATED 220 grams of a linear nonylphenol were mixed in an autoclave with 1.1 grams of NaOH and reacted with 396 grams of ethylene oxide (EO) fed into the autoclave over a four-hour period at a temperature of 150° C. and a pressure of 50 psi. Ppressure and temperature were controlled by EO charge rate and rate of flow of cooling water. After all the oxide was charged, the reaction was held for one hour and the autoclave was then placed under a 50 mm vacuum for thirty minutes, and the vacuum was broken with nitrogen. The resulting 9 mole ethoxylate of nonylphenol was then cooled to 50° C. and the catalyst was neutralized with HCl to a pH of between 6 and 7, inclusive.

In the autoclave, the resulting 617.1 grams of product was mixed with 250 grams of dioxane and 4 grams of a finely divided rhodium on carbon (10% rhodium) and then the vessel was purged with nitrogen. Hydrogen was charged until the pressure reached 100 psi and then the autoclave was heated to 50° C. With moderate agitation the hydrogenation process continued until no more hydrogen was taken up. This reaction took approximately nine and one-half hours. The product was recovered by filtering out the catalyst under nitrogen and then vacuum stripping off the volatile solvent. A water white liquid identified as nonylcyclohexyl alcohol with 9 moles of EO (NCH-9) was produced with less than 100 ppm of free nonylcyclohexanol and at least 91% saturation of the aromatic rings.

Typical uses for NCH-9 are as an emulsifier, wetting agent for textiles, a detergent, a scouring agent, and a hard surface cleaner.

EXAMPLE 2

TRISTYRENATED PHENOL (EO)$_{15}$, HYDROGENATED 406 grams of a tristyrenated phenol were mixed in an autoclave with 2.1 grams of NaOCH$_3$ and reacted with 660 grams of ethylene oxide (EO) fed into the autoclave over a six-hour period at a temperature of 160° C. and a pressure of 75 psi. Pressure and temperature were controlled by EO charge rate and rate of flow of cooling water. After all the oxide was charged, the reaction was held for one hour and then the autoclave was placed under a 50 mm vacuum for thirty minutes and the vacuum was broken with nitrogen. The resulting 15 mole ethoxylate of tristyrenated phenol was then cooled to 50° C. and the NaOCH$_3$ catalyst was neutralized with HCl to a pH between 6 and 7, inclusive.

In the autoclave, the resulting 1068.1 grams of product was mixed with 500 grams of dioxane and 8 grams of a finely divided rhodium on carbon (10% rhodium) and then the vessel was purged with nitrogen. Hydrogen was charged until the pressure reached 100 psi and then the autoclave was heated to 50° C. With moderate agitation the hydrogenation process continued until no more hydrogen was taken up. This reaction took approximately twelve hours. The product was recovered by filtering out the catalyst under nitrogen and then vacuum stripping off the volatile solvent. A water white liquid identified as tri(ethylcyclohexyl) cylcohexyl alcohol with 15 moles of EO (TECCH-15) was produced with less than 1000 ppm of free tri(ethylcyclohexyl) cylcohexyl alcohol and 76% saturation of the aromatic rings.

Typical uses of TECCH-15 are as a dispersant for a dispersed dye, for herbicides, or for insecticides.

EXAMPLE 3

DISTEARYL PHENOL (EO)$_6$ (PO)$_{15}$, HYDROGENATED 598 grams of a distearyl phenol were mixed in an autoclave with 3.5 grams of NaOH and reacted with 264 grams of ethylene oxide (EO) fed into the autoclave over a two-hour period at a temperature of 160° C. and a pressure of 75 psi and 885 grams of propylene oxide (PO) fed into the autoclave over a nine-hour period at a temperature of 120° C. and a pressure of 40 psi. Pressure and temperature were controlled by EO and PO charge rates and rate of flow of cooling water. After all the oxide was charged, the reaction was held for one hour and then the autoclave was placed under a 50 mm vacuum for thirty minutes and the vacuum was broken with nitrogen. The resulting 6 mole ethoxylate, 15 mole propoxylate of distearyl phenol was then cooled to 50° C. and the NaOH catalyst was neutralized with acetic acid to a pH between 6 and 7, inclusive.

In the autoclave, the resulting 1750.5 grams of product was mixed with 750 grams of dioxane and 12 grams of a finely divided rhodium on carbon (10% rhodium) and then the vessel was purged with nitrogen. Hydrogen was charged until the pressure reached 100 psi and then the autoclave was heated to 70° C. With moderate agitation the hydrogenation process continued until no more hydrogen was taken up. This reaction took approximately twelve hours. The product was recovered by filtering out the catalyst under nitrogen and then vacuum stripping off the volatile solvent. A water white liquid identified as distearyl cylcohexyl alcohol with 6 moles of EO and 15 moles of PO (DSCH-6,15) was produced with less than 100 ppm free distearyl cylcohexyl alcohol and at least 92% saturation of the aromatic rings.

Uses for products such as DSCH-6,15 are as thermally stable lubricants for high temperature processes, low foam emulsifiers for saturated C16–C22 esters, or emollients for cosmetic creams.

EXAMPLE 4

NONYLPHENOL (EO)$_{1.5}$, HYDROGENATED, (EO)$_5$(peaked)

220 grams of a linear nonylphenol were mixed in an autoclave with 0.4 grams of NaOH and reacted with 66 grams of ethylene oxide (EO) fed into the autoclave over a four-hour period at a temperature of 150° C. and a pressure of 50 psi. Pressure and temperature were controlled by EO charge rate and rate of flow of cooling water. After all the oxide was charged, the reaction was held for one hour and then the autoclave was placed under a 50 mm vacuum for thirty minutes and the vacuum was broken with nitrogen. The resulting 1.5 mole ethoxylate of nonylphenol was then cooled to 50° C. and the catalyst was neutralized with HCl to a pH between 6 and 7, inclusive.

In the autoclave, the resulting 286.4 grams of product was mixed with 125 grams of dioxane and 2 grams of a finely divided rhodium on carbon (10% rhodium) and then the vessel was purged with nitrogen. Hydrogen was charged until the pressure reached 100 psi and the autoclave was heated to 50° C. With moderate agitation the hydrogenation process continued until no more hydrogen was taken up. This reaction took approximately twelve hours. The product was recovered by filtering out the catalyst under nitrogen and then vacuum stripping off the volatile solvent. A water white liquid identified as nonylcyclohexyl alcohol with 1.5 moles of EO (NCH-1.5) was produced with less than 100 ppm of free nonylcyclohexanol and at least 92% saturation of the aromatic rings.

The resulting 292.4 grams of NCH-1.5 was then mixed with 1.9 grams CaO in an autoclave and reacted with 220 grams of ethylene oxide (EO) fed into the autoclave over a six-hour period at a temperature of 150° C. and a pressure of 50 psi. Pressure and temperature were controlled by EO charge rate and rate of flow of cooling water. After all the oxide was charged, the reaction was held for one hour and the autoclave was placed under a 50 mm vacuum for thirty minutes and the vacuum was broken with nitrogen. The resulting 5 mole ethoxylate of nonylcyclohexyl alcohol (NCH-5 pk) was then cooled to 50° C. and the catalyst was neutralized with HCl to a pH balance between 6 and 7, inclusive.

Typical uses for NCH-5 pk are for liquid, high actives based systems such as liquid laundry detergent, low level emulsification system for coning oils used in textiles and to improve wetting and penetration of textiles.

EXAMPLE 5

4-NONYL, 2-TERT BUTYLPHENOL $(EO)_{15}$ HYDROGENATED WITH CIS SPECIFIC CATALYST 227 grams of a 4-nonyl, 2-tert butylphenol were mixed in an autoclave with 0.6 grams of NaOH and reacted with 176 grams of ethylene oxide (EO) fed into the autoclave over a three-hour period at a temperature of 150° C. and a pressure of 50 psi. Pressure and temperature were controlled by EO charge rate and rate of flow of cooling water. After all the oxide was charged, the reaction was held for one hour and the autoclave was placed under a 50 mm vacuum for thirty minutes and the vacuum was broken with nitrogen. The resulting 4 mole ethoxylate of 4-nonyl, 2-tert butylphenol was then cooled to 50° C. and the catalyst was neutralized with phosphoric acid HCl to a pH between 6 and 7, inclusive.

A hydrogenation catalyst that would result in a product of high cis isomer content was prepared by taking 10 grams of 5% (by weight) rhodium on a commercial alumina support, 0.920 grams of $BF_3O(C_2H_5)_2$ and added to 60 ml of ethyl acetate in a 100 ml. flask under nitrogen. The flask was stirred by means of a rotary evaporator at 45° C. for two hours. The flask was then placed under a 10 mm vacuum until all of the solvent was removed. The solid product was maintained under nitrogen until ready for use.

In the autoclave, the resulting 453.6 grams of the 4 mole ethoxylate of 4-nonyl, 2-tert butylphenol was mixed with 125 grams of dioxane and 3.5 grams of the above-prepared catalyst and then the vessel was purged with nitrogen. Hydrogen was charged until the pressure reached 100 psi and then the autoclave was heated to 100° C. With moderate agitation the hydrogenation process continued until no more hydrogen was taken up. This reaction took approximately 4.5 hours. The product was recovered by filtering out the catalyst under nitrogen and then vacuum stripping off the volatile solvent. A water white liquid identified as 4-nonyl, 2-tert butylcyclohexyl alcohol with 4.0 moles of EO (NTBCH-4) was produced with less than 150 ppm of free 4-nonyl, 2-tert butylcyclohexyl alcohol and at least 81% saturation of the aromatic rings.

Typical uses for NTBCH-4 are as emulsifiers for pesticide formulations, and thermally stable lubricants and emulsifiers for high temperature processes.

EXAMPLE 6

DIBUTYLPHENOL $(EO)_4$, HYDROGENATED 207 grams of a dibutylphenol were mixed in an autoclave with 0.6 grams of NaOH and reacted with 176 grams of ethylene oxide (EO) fed into the autoclave over a three-hour period at a temperature of 150° C. and a pressure of 50 psi. Pressure and temperature were controlled by EO charge rate and rate of flow of cooling water. After all the oxide was charged, the reaction was held for one hour and then the autoclave was placed under a 50 mm vacuum for thirty minutes and the vacuum was broken with nitrogen. The resulting 4 mole ethoxylate of dibutylphenol was then cooled to 50° C. and the catalyst was neutralized with phosphoric acid HCl to a pH between 6 and 7, inclusive.

A hydrogenation catalyst was prepared by taking 24.4 grams of ruthenium trichloride hydrate (10 grams of ruthenium) added to 1000 grams of tetrahydrofuran under nitrogen with 75 grams of magnesium powder and refluxed for five hours. The mixture was subsequently filtered under nitrogen.

In the autoclave, the resulting 383.6 grams of the 4 mole ethoxylate of dibutylphenol was mixed with 200 grams of tetrahydrofuran and 60 grams of the above-prepared catalyst solution and then the vessel was purged with nitrogen. Hydrogen was charged until the pressure reached 130 psi and then the autoclave was heated to 80° C. With moderate agitation the hydrogenation process continued until no more hydrogen was taken up. This reaction took approximately 4.5 hours. The product was recovered by filtering out the catalyst under nitrogen and then vacuum stripping off the volatile solvent. A water white liquid identified as dibutyl-cyclohexyl alcohol with 4.0 moles of EO (DBCH-4) was produced with less than 100 ppm of free dibutylcyclohexyl alcohol and at least 81% saturation of the aromatic rings.

When 0.2% DBCH-4 has dissolved in distilled water, and draves wetting test performed, typical wetting speeds were in the range of 6 to 8 seconds.

EXAMPLE 7

NONYLPHENOL$(EO)_{200}$, HYDROGENATED 220 grams of a linear nonylphenol were mixed in an autoclave with 20 grams of NaOH and reacted with 8800 grams of ethylene oxide (EO) fed into the autoclave over a nine-hour period at a temperature of 150° C. and a pressure of 75 psi. Pressure and temperature were controlled by EO charge rate and rate of flow of cooling water. After all the oxide was charged, the reaction was held for one hour and then the autoclave was placed under a 50 mm vacuum for thirty minutes and the vacuum was broken with nitrogen. The resulting 200 mole ethoxylate of nonylphenol was then cooled to 50° C. and the catalyst was neutralized with HCl to a pH between 6 and 7, inclusive.

In the autoclave, the 9040 grams of resulting product were mixed with 50 grams of a finely divided nickel catalyst and the vessel was purged with hydrogen and sealed. Hydrogen was then charged until the pressure reached 1000 psi and then the autoclave was heated to 200° C. With moderate agitation the hydrogenation process continued at pressures of 1000 psi until no more hydrogen was taken up. This reaction took approximately five hours. The product was recovered by filtering out the catalyst under nitrogen. A water white liquid identified as nonyl cyclohexyl alcohol with 200 moles of EO (NCH-200) was produced with no detectable levels of free nonylcyclohexanol and at least 73% saturation of the aromatic rings.

Typical uses for NCH-200 are as plasticizers for thermoplastics such as nylon, polymerization surfactant for polymers such as vinyl acetate or polyacrylates or emulsifiers and stabilizer for floor waxes and polishes.

EXAMPLE 8

PHENOL $(PO)_{70}$, HYDROGENATED 94 grams of phenol are mixed in an autoclave with 8 grams of NaOH and reacted with 4130 grams of propylene oxide (PO) fed into the autoclave over a 12-hour period at a temperature of 130° C. and a pressure of 50 psi. Pressure and temperature are controlled by PO charge rate and rate of flow of cooling water. After all the oxide is charged, the reaction is held for one hour and then the autoclave is placed under a 50 mm vacuum for thirty minutes and the vacuum is broken with nitrogen. The resulting 70 mole propoxylate of phenol is then cooled to 50° C. and the catalyst is neutralized with HCl to a pH between 6 and 7, inclusive. Then hydrogenation of the resulting propoxylated phenol is conducted by a conventional method. It is expected that this would result in a white water liquid identifiable as cyclohexyl alcohol with 70 moles of PO (CH-70-P), with free cyclohexyl alcohol less than about 2% and at least 90% saturation of the aromatic ring.

Typical uses for CH-70-P are as de-emulsifiers and defoamers.

EXAMPLE 9

DIAMYLPHENOL $(EO)_6(BO)_6$, HYDROGENATED 234 grams of diamylphenol are mixed in an autoclave with 0.2 grams of NaOH and reacted with 234 grams of ethylene oxide (EO) fed into the autoclave over a two-hour period at a temperature of 150° C. and a pressure of 75 psi. Pressure and temperature are controlled by EO charge rate and rate of flow of cooling water. This is then followed by the addition of 432 grams of butylene oxide (BO) at a temperature of 130° C. and a pressure of 20 psi. After all the oxide is charged, the reaction is held for one hour and then the autoclave is placed under a 50 mm vacuum for thirty minutes and the vacuum is broken with nitrogen. The resulting 6 mole ethoxylate, 6 mole butoxylate of diamylphenol is then cooled to 50° C. and the catalyst is neutralized with HCl to a pH between 6 and 7, inclusive. The hydrogenation of the alkoxylated diamylphenol is conducted by a conventional method. It is expected that a white water liquid identified as diamylcyclohexyl alcohol with 6 moles of EO and 6 moles of BO (DACH-6,6-B) would result. There should be less than 2% free diamylcyclohexyl alcohol at least 90% saturation of the aromatic ring.

Typical uses for DACH-6,6-B are as a lubricant or as an anti-tacking agent for drum dryers and pad application equipment for polymers such as polyacrylates or self-crosslinking polymers.

EXAMPLE 10

LINEAR C30 PHENOL $(EO)_{10}$, HYDROGENATED 515 grams of a linear C-30 phenol are heated to 60° C. and mixed in an autoclave with 2 grams of NaOH and reacted with 440 grams of ethylene oxide (EO) fed into the autoclave over a four-hour period at a temperature of 150° C. and a pressure of 75 psi. Pressure and temperature are controlled by EO charge rate and rate of flow of cooling water. After all the oxide is charged, the reaction is held for one hour and then the autoclave is placed under a 50 mm vacuum for thirty minutes and the vacuum is broken with nitrogen. The resulting 10 mole ethoxylate of C-30 phenol is then cooled to 50° C. and the catalyst is neutralized with HCl to a pH between 6 and 7, inclusive. The hydrogenation of the resulting ethoxylated C30 phenol is conducted by a conventional method. This is expected to result in a white water liquid identified as (C-30 cyclohexyl alcohol with 10 moles EO (C-30, CH-10), less than 2% free cyclohexyl alcohol, and greater than about 90% saturation of the aromatic ring.

Typical uses for C-30 CH-10 are as process lubricants, as an emulsifier for triglycerides and esters such as pentaerythritol tetrastearate or as an emollient for cosmetic creams.

EXAMPLE 11

TRIISO-OCTYLDECYLPHENOL $(EO)_3$, HYDROGENATED 851 grams of a triiso-octyldecylphenol was melted at 70° C. in an autoclave, mixed with 3.5 grams of KOH and reacted with 132 grams of ethylene oxide (EO) fed into the autoclave over a two-hour period at a temperature of 160° C. and a pressure of 75 psi. Pressure and temperature were controlled by EO charge rate and rate of flow of cooling water. After all the oxide was charged, the reaction was held for one hour and the autoclave was placed under a 50 mm vacuum for thirty minutes and the vacuum was broken with nitrogen. The resulting 3 mole ethoxylate was then cooled to 50° C. and the KOH catalyst was neutralized with acetic acid to a pH between 6 and 7, inclusive.

In the autoclave, the resulting 986.5 grams of product was mixed with 750 grams of dioxane and 12 grams of a finely divided rhodium on carbon (10% rhodium) and the vessel was purged with nitrogen. Hydrogen was then charged until the pressure reached 100 psi and the autoclave was heated to 70° C. With moderate agitation the hydrogenation process continued until no more hydrogen was taken up. This reaction took approximately six hours. The product was recovered by filtering out the catalyst under nitrogen and then vacuum stripping off the volatile solvent. A white solid product identified as triisooctyldecylcyclohexyl alcohol with 3 moles of EO(TODCH-3) was produced, with less than 3000 ppm of free triisooctyldecylcyclohexyl alcohol and at least 79% saturation of the aromatic rings.

Typical uses of TODCH-3 are as a mold release for thermoresins such as polycarbonate or polyester.

EXAMPLE 12

NONYL CYCLOHEXANOL ETHOXYLATED TO $(EO)_9$

A hydrogenation catalyst was prepared by taking 24.4 grams of ruthenium trichloride hydrate (10 grams of ruthenium) added to 1000 grams of tetrahydrofuran under nitrogen with 75 grams of magnesium powder and refluxed for five hours. The mixture was subsequently filtered under nitrogen.

In the autoclave, 300 grams of a linear nonylphenol was mixed with 200 grams of tetrahydrofuran and 50 grams of the above-prepared catalyst solution and the vessel was purged with nitrogen. Hydrogen was then charged until the pressure reaches 130 psi and the autoclave heated to 8° C. With moderate agitation the hydrogenation process continued until no more hydrogen was taken up. This reaction took approximately eight hours. The product was recovered by filtering out the catalyst under nitrogen and then vacuum stripping off the volatile solvent. A water white liquid identified as nonylcyclohexanol was produced with 2.8% unsaturation.

The resulting 226 grams of linear nonylcyclohexanol was mixed in an autoclave with 1.1 grams of NaOH and then reacted with 396 grams of ethylene oxide (EO) fed into the autoclave over a six-hour period at a temperature of 150° C. and a pressure of 50 psi. Pressure and temperature were controlled by EO charge rate and rate of flow of cooling water. After all the oxide was charged, the reaction was held for one hour and then the autoclave was placed under a 50 mm vacuum for thirty minutes and the vacuum was broken with nitrogen. The resulting 9 mole ethoxylate of nonylcyclohexanol was then cooled to 50° C. and the catalyst was neutralized with HCl to a pH between 6 and 7, inclusive. A water white liquid identified as nonylcyclohexyl alcohol with 9 moles of EO(NCH-9b) was produced with 26% free nonylcyclohexanol and less than 1% unsaturation.

This example was prepared to demonstrate the results obtained when a nonylphenol is first hydrogenated and then ethoxylated. The amount of free nonylcyclohexanol resulting from this method results in poor performance, cost, etc., as discussed above.

PREPARATION OF POLYETHYLENE WAX EMULSION

An evaluation of the emulsification properties of NCH-9 of the present invention, prepared by the method of the present invention, NCH-9b as prepared in Example 12, and commercial ethoxylated nonylphenol and alkyl alcohols, ethoxylated with 9 moles EO was conducted. A polyethylene wax emulsion was prepared with Easman polyethylene wax, KOH, NaCl, water, and emulsifier. The materials were mixed together and then heated in a sealed vessel to 130° C., held for thirty minutes and then rapidly cooled to 50° C. The quantities used and results obtained are set forth in Table 2. These results show that NCH-9 produces an emulsion equivalent to the nonylphenol-9, better than alkoxylated alkyl alcohols and far superior to the NCH-9b.

TABLE 2

| EMULSIFICATION PROPERTIES | | | | | | |
|---|---|---|---|---|---|---|
| Polyethylene Wax (Eastman E 10) | 200.0 gr | 200.0 gr | 200.0 gr | 200.0 gr | 200.0 gr | 200.0 gr |
| KOH | 3.0 gr | 3.0 gr | 3.0 gr | 3.0 gr | 3.0 gr | 3.0 gr |
| NaCl | 0.2 gr | 0.2 gr | 0.2 gr | 0.2 gr | 0.2 gr | 0.2 gr |
| Water | 746.8 gr | 746.8 gr | 746.8 gr | 746.8 gr | 746.8 gr | 746.8 gr |
| NCH-9 | 50.0 gr | | | | | |
| NCH-9b | | 50.0 gr | | | | |
| Nonyl phenol-9 EO (Rhone Poulenc) | | | 50.0 gr | | | |
| C12–C15-9EO (Shell Chemicals) | | | | | | 50.0 gr |
| C12–C14-9EO (Vista Chemicals) | | | | 50.0 gr | | |
| C12–C14-9EO (Narrow range) (Vista Chemicals) | | | | | 50.0 gr | |
| Appearance (initial) | translucent emulsion | milky, large particles unstable | translucent emulsion | very hazy emulsion | slightly hazy emulsion | very hazy emulsion |
| Appearance (24 hours) | translucent emulsion | | translucent emulsion | layer of particles on surface | hazy emulsion | slightly unstable |

FORMULATION OF FIBER LUBRICANT

A comparison of the formulation properties of NCH-9 of the present invention prepared by the method of the present invention, NCH-9b prepared in Example 12, and commercial ethoxylated nonylphenols and alkyl alcohols ethoxylated with 9 moles EO was conducted. A typical tridecyl stearate-based lubricant was formulated with tridecyl stearate, phosphate ester, KOH, water, and the surfactant under evaluation.

To prepare the lubricant, the surfactant and the phosphate ester were charged and mixed. Then the KOH was slowly charged and the mix heated to 50° C. Then water was charged and mixed, followed by a charge of tridecyl stearate and mixing for thirty minutes. The quantities used and the results noted are set forth in Table 3.

These results show that the NCH-9 is equivalent to the commercial nonylphenol-9 in formulating, emulsification, and odor and outperformed the NCH-9b in all aspects.

TABLE 3

EVALUATING FORMULATION PROPERTIES

| | | | | | | |
|---|---|---|---|---|---|---|
| Tridecyl Stearate (Inolex) | 650.0 gr | 650.0 gr | 650.0 gr | 650.0 gr | 650.0 gr | 650.0 gr |
| Rhodaphos RB 610 (Rhone Poulenc) phosphate ester | 8.0 gr | 8.0 gr | 8.0 gr | 8.0 gr | 8.0 gr | 8.0 gr |
| KOH (45%) | 15.0 gr | 15.0 gr | 15.0 gr | 15.0 gr | 15.0 gr | 15.0 gr |
| Water | 5.0 gr | 5.0 gr | 5.0 gr | 5.0 gr | 5.0 gr | 5.0 gr |
| NCH-9 | 25.0 gr | | | | | |
| NCH-9b | | 25.0 gr | | | | |
| Nonyl phenol-9 EO (Rhone Poulenc) | | | 25.0 gr | | | |
| C12–C15-EO (Shell Chemicals) | | | | | | 25.0 gr |
| C12–C14-9 EO (Vista Chemicals) | | | | 25.0 gr | | |
| C12–C14-9 EO (Narrow range) (Vista Chemicals) | | | | | 25.0 gr | |
| Product appearance (initial/25 C.) | Clear | Cloudy | Clear | Cloudy | Hazy | Cloudy |
| Product appearance (24 hours/25 C.) | Clear | Split | Clear | Semi-solid, clear on top | Semi-solid, clear on top | Hazy, viscous |
| 10% emulsion/24 hours | Stable | Split | Stable | Creaming on top | Slight creaming on top | Slight separation |
| Product odor* | Typical | Strong, offensive | Typical | Slightly stronger | Typical | Slightly stronger |

*Typical odor would be a standard odor without emulsifier. (Note phosphate ester odor fairly strong of tridecyl alcohol.)

Surfactants were evaluated as wetting agents using a 0.2% concentration at room temperature using standard method AATCC # 17-1994. The results of this wetting agent test are set forth in Table 4.

NCH-9 shown to be equivalent to nonylphenol-9 and slightly better than alkoxylated alcohol ethoxylates, while the NCH-9b did not wet at all.

TABLE 4

EVALUATION OF WETTING PROPERTIES OF TEXTILES

| (Supplier) Materials Tested | Results |
|---|---|
| NCH-9 | 9.2 sec |
| NCH-9b | >300 sec |
| (Rhone Poulenc) nonylphenol –9 EO | 12.1 sec |
| (Shell Chemicals) C12–C15 –9 EO | 18.3 sec |
| (Vista Chemicals) C12–C14 –9 EO | 19.4 sec |
| (Vista Chemicals) C12–C14 –9 EO (narrow range) | 16.0 sec |

The detergent properties of NCH-9 of the present invention, prepared by the method of the present invention, were compared with those of NCH-9b prepared in accordance with Example 12, and commercial nonylphenol and alkyl alcohols ethoxylated with 9 moles EO. Test solutions were prepared and added to steel launderometer beakers along with 50 steel balls. A 10 gram section of a specially soiled 100% cotton fabric (from test fabrics) was placed in each steel beaker. The steel beakers were sealed and placed in the launderometer. The launderometer was heated to 160° F. and held for thirty minutes. Samples were removed from the beakers, rinsed, hung to air dry for 12 hours, and then rated. The ratings for each surfactant are set forth in Table 5. NCH-9 detergency was shown to be equivalent to that of nonylphenol-9 and slightly better than standard alkoxylated alkyl alcohols, while NCH-9b possessed poor detergency.

TABLE 5

EVALUATION OF DETERGENCY

| | | | | | | |
|---|---|---|---|---|---|---|
| Water | 494.0 gr | 494.0 gr | 494.0 gr | 494.0 gr | 494.0 gr | 494.0 gr |
| NaOH (50%) | 1.0 gr | 1.0 gr | 1.0 gr | 1.0 gr | 1.0 gr | 1.0 gr |
| NCH-9 | 5.0 gr | | | | | |
| NCH-9b | | 5.0 gr | | | | |
| nonylphenol-9 EO (Rhone Poulenc) | | | 5.0 gr | | | |
| C12–C15-9 EO (Shell Chemicals) | | | | | | 5.0 gr |
| C12–C14-9 EO (Vista Chemicals) | | | | 5.0 gr | | 5.0 gr |
| C12–C14-9 EO (Narrow range) (Vista Chemicals) | | | | | 5.0 gr | |
| *Fabric Rating | 2.5 | 5.0 | 2.5 | 3.5 | 3.0 | 3.5 |

*Rating:
5 = no soil removal
1 = total soil removal

It will therefore be readily understood by those persons skilled in the art that the present invention is susceptible of broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. A process of preparing a cyclohexanol alkoxylate, comprising the steps of reacting a phenol with an alkylene oxide to alkoxylate the phenol and form a polyoxyalkylene ether group on the phenol, and hydrogenating the resulting alkoxylated phenol in the presence of a catalyst to form an alkoxylated cyclohexanol.

2. The process of claim 1, wherein the phenol and the resulting cyclohexanol have at least one alkyl group on the ring.

3. The process of claim 1, wherein reacting the phenol with the alkylene oxide results in less than about 2% free phenol.

4. The process of claim 3, wherein after hydrogenation, the alkoxylated cyclohexanol has less than about 2 percent residual free phenol.

5. The process of claim 1, wherein the alkylene oxide is selected from the group consisting of ethylene oxide, propylene oxide, and butylene oxide.

6. The process of claim 5, wherein the alkylene oxide is ethylene oxide.

7. The process of claim 1, wherein hydrogenating the alkoxylated phenol results in at least about 90% saturation of the phenol aromatic ring.

8. The process of claim 1, further comprising the step of further alkoxylating the alkoxylated cyclohexanol.

9. A process as defined in claim 2, wherein said alkyl group is linear.

10. A process as defined in claim 2, wherein said alkyl group is branched.

11. A process as defined in claims 1, wherein said catalyst is contained on an inert carrier.

12. A process as defined in claim 11, wherein said inert carrier comprises aluminum or carbon.

13. A process as defined in claim 2, wherein said alkyl cyclohexanol alkoxylate comprises an octyl cyclohexanol alkoxylate or a nonyl cyclohexanol alkoxylate.

14. A process as defined in claim 2, wherein said alkyl cyclohexanol alkoxylate comprises an alkoxylated nonylcyclohexyl alcohol.

15. A process as defined in claim 2, wherein said alkyl cyclohexanol alkoxylate comprises an alkoxylated tri (ethylcyclohexyl) cyclohexyl alcohol.

16. A process as defined in claim 2, wherein said alkyl cyclohexanol alkoxylate comprises an alkoxylated distearyl cyclohexyl alcohol.

17. A process as defined in claim 2, wherein said alkyl cyclohexanol alkoxylate comprises an alkoxylated 4-nonyl, 2-tert butylcyclohexyl alcohol.

18. A process as defined in claim 2, wherein said alkyl cyclohexanol alkoxylate comprises an alkoxylated dibutyl-cyclohexyl alcohol.

19. A process as defined in claim 2, wherein said alkyl cyclohexanol alkoxylate comprises an alkoxylated alkyl cyclohexyl alcohol.

20. A process as defined in claim 2, wherein said alkyl cyclohexanol alkoxylate comprises an alkoxylated diamyl-cyclohexyl alcohol.

21. A process as defined in claim 2, wherein said alkyl cyclohexanol alkoxylate comprises an alkoxylated triisooctyldecylcyclohexyl alcohol.

22. A process as defined in claim 1, wherein said catalyst comprises a rhodium catalyst or a ruthenium catalyst.

23. A process for of preparing an alkyl cyclohexanol alkoxylate of the formula:

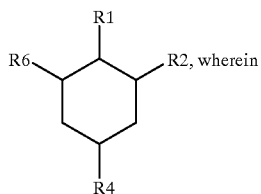

R2, R4, and R6 are each independently selected from the group consisting of hydrogen; an alkyl group or mixtures thereof having between one and thirty carbons; a cyclohexyl group; and an etheneaychohexyl group and R1 is a polyoxyalkylene either having the formula:

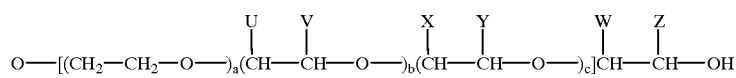

Where:
U is hydrogen or $CH_3$—,
V is $CH_3$— if U is hydrogen, or hydrogen if U is $CH_3$—,
X is hydrogen or $CH_3CH_2$—,
Y is $CH_3CH_2$— if X is hydrogen, or hydrogen if X is $CH_3CH_2$—,
W is hydrogen, $CH_3$—, or $CH_3CH_2$—,
Z is hydrogen, $CH_3$—, or $CH_3CH_2$— if W is a hydrogen, or hydrogen if W is $CH_3$— or $CH_3CH_2$—,
a is an integer between 0 and 200,
b is an integer between 0 and 100,
c is an integer between 0 and 100, and
a+b+c=2–200, comprising the steps of alkoxylating an alkyl phenol by reacting

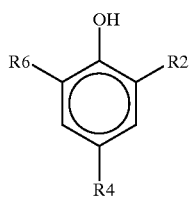

R2, R4, and R6 are each independently selected from the group consisting of hydrogen; an alkyl, alkenyl, or alkynyl group or mixtures thereof having between one and thirty carbons; —$C_6H_5$; and —$C_8H_9$, with an alkylene oxide selected from the group consisting of ethylene oxide, propylene oxide, butylene oxide, and mixtures thereof to alkoxylate the phenol, resulting in a compound having the formula:

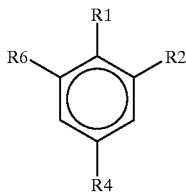

R2, R4, and R6 are each independently selected from the group consisting of hydrogen; an alkyl, alkenyl, or alkynyl group or mixtures thereof having between one and thirty carbons; —$C_6H_5$; and —$C_8H_9$, R1 as recited above; and hydrogenating the resulting alkoxylated alkyl phenol in the presence of a catalyst;

wherein the alkoxylation step results in less than 2% free alkyl phenol and the hydrogenation step results in at least about 90% saturation of the aromatic ring.

24. A process as defined in claim 23, wherein said hydrogenation step takes place at a pressure of at least 50 psi.

25. A process as defined in claim 23, wherein said hydrogenation step takes place at a pressure of at least 1,000 psi.

26. A process as defined in claim 23, wherein said hydrogenation step takes place at a temperature from about 25° C. to about 200° C.

27. A process as defined in claim 24, wherein said hydrogenation step takes place at a temperature from about 25° C. to about 200° C.

28. A process as defined in claim 25, wherein said hydrogenation step takes place at a temperature of from about 25° C. to about 200° C.

29. A process as defined in claim 23, wherein said catalyst is present in an amount of from about 0.001 percent to about 1 percent by weight based upon the weight of said alkoxylated alkyl phenol.

30. A process as defined in claim 24, wherein said catalyst is present in an amount from about 0.001 percent to about 1 percent by weight based upon the weight of said alkoxylated alkyl phenol.

31. A process as defined in claim 27, wherein said catalyst is present in an amount of from about 0.001 percent to about 1 percent by weight based upon the weight of said alkoxylated alkyl phenol.

32. A process as defined in claim 23, wherein said catalyst is contained on an inert carrier.

33. A process as defined in claim 32, wherein said inert carrier comprises carbon.

34. A process as defined in claim 27, wherein said catalyst is contained on an inert carrier.

35. A process as defined in claim 34, wherein said inert carrier comprises carbon.

36. A process as defined in claim 28, wherein said catalyst is contained on an inert carrier.

37. A process as defined in claim 36, wherein said inert carrier comprises carbon.

38. A process as defined in claim 23, wherein after hydrogenation, the alkoxylated alkyl cyclohexanol has less than about 2% residual free alkyl phenol.

39. A process as defined in claim 23, wherein the alkylene oxide is ethylene oxide.

40. A process as defined in claim 23, further comprising the step of further alkoxylating the alkoxylated cyclohexanol.

41. A process as defined in claim 23, wherein said hydrogenation step takes place in the presence of a solvent.

42. A process as defined in claim 41, wherein said solvent comprises a material selected from the group consisting of dioxane and tetrahydrofuran.

43. A process as defined in claim 23, wherein hydrogenating the resulting alkoxylated alkyl phenol results in at least about 90 percent saturation of the phenolic aromatic ring.

44. A process as defined in claim 23, wherein said catalyst comprises a rhodium catalyst or a ruthenium catalyst.

45. A process for preparing a surfactant, comprising the steps of reacting a phenol with an alkylene oxide to alkoxylate the phenol and form a polyoxyalkylene ether group on the phenol, and hydrogenating the resulting alkoxylated phenol in the presence of a catalyst to form an alkoxylated cyclohexanol.

46. The process of claim 45, wherein the phenol and the resulting cyclohexanol have at least one alkyl group on the ring.

47. The process of claim 45, wherein after hydrogenation, the alkoxylated cyclohexanol has less than about 2% residual free phenol.

48. The process of claim 45, wherein the alkylene oxide is selected from the group consisting of ethylene oxide, propylene oxide and butylene oxide.

49. The process of claim 48, wherein the alkylene oxide is ethylene oxide.

50. The process of claim 45, wherein hydrogenating the resulting alkoxylated phenol results in at least about 90% saturation of the phenol aromatic ring.

51. The process of claim 45, further comprising the step of further alkoxylating the alkoxylated cyclohexanol.

52. A process as defined in claim 45, wherein said catalyst comprises a rhodium catalyst or a ruthenium catalyst.

* * * * *